(12) United States Patent
Voorhees et al.

(10) Patent No.: US 6,799,119 B1
(45) Date of Patent: Sep. 28, 2004

(54) METHOD FOR DETECTION OF BIOLOGICAL RELATED MATERIALS USING BIOMARKERS

(75) Inventors: Kent J. Voorhees, Golden, CO (US); Francisco Basile, Golden, CO (US)

(73) Assignee: Colorado School of Mines, Golden, CO (US)

( * ) Notice: Subject to any disclaimer, the term of this patent is extended or adjusted under 35 U.S.C. 154(b) by 0 days.

(21) Appl. No.: 09/570,676

(22) Filed: May 15, 2000

(51) Int. Cl.[7] ..................... G01N 33/48; G01N 33/50; G01N 31/00; G06F 19/00; C12Q 1/68
(52) U.S. Cl. ..................... 702/19; 702/20; 702/22; 435/4; 435/6
(58) Field of Search ............................. 702/19, 20, 22

(56) References Cited

U.S. PATENT DOCUMENTS 5,101,105 A * 3/1992 Fenselau et al. ............ 250/281

OTHER PUBLICATIONS

Goodacre et al. Journal of Applied Bacteriology, 1994, 76, 124–134.*
Gharaibeh et al. Anal. Chem. 1996, 68:2805–2810.*
Deluca et al. Anal. Chem. 1986, 58, 2439–2442, see abstract.*
Yates, III et al. Anal. Chem. 1998, 70, 3557–3565.*

* cited by examiner

Primary Examiner—John Brusca
Assistant Examiner—Shubo Zhou
(74) Attorney, Agent, or Firm—Holland & Hart LLP; Christopher J. Kulish, Esq.

(57) ABSTRACT

The present invention relates to a method for the detection of biological agents and, in particular, biological agents that may present a health hazard. In one embodiment, the invention identifies the unidentified biological agent, assesses the reliability of the identification, and if determined to be reliable, outputs the identification. Initially, data that relates to the biological composition of an unidentified biological agent is received. The data is then analyzed with a machine learning procedure to identify the unidentified biological agent in the sample. The reliability of the identification is then assessed with, for example, an analysis of MS/MS data on the unidentified biological agent. If the identification is found to be reliable, the identification is output.

17 Claims, 9 Drawing Sheets

US 6,799,119 B1

METHOD FOR DETECTION OF BIOLOGICAL RELATED MATERIALS USING BIOMARKERS

STATEMENT REGARDING FEDERALLY SPONSORED RESEARCH

The invention was made with Government support under Contract No. DAAM01-95-C-0068 awarded by the Army. The Government has certain rights in the invention.

FIELD OF THE INVENTION

The present invention relates to the detection of biological related materials and, in particular, the detection of biological related materials that may present a health risk to a population that is or may be exposed to such materials.

BACKGROUND OF THE INVENTION

There are many types of biological related materials that pose health risks to populations (human, animal or plant) that may be exposed to such materials. Among the biological related materials that pose health risks are bacteria, viruses, and toxins (which are chemicals that are derived from biological entities). Among the more well known bacteria that present health risks to humans are *Bacillus anthracis* (anthrax), *Yersinia pestis* (plague) and *Vibrio cholerae* (cholera). Examples of viruses that pose health risks to humans are the small pox, Ebola, Marburg and Hanta viruses. Toxins that present a danger to humans include polyethers, proteins and mycotoxins.

Presently, there are a number of techniques available for detecting biological related materials (hereinafter referred to as "biological agents"). One traditional technique is to: (1) obtain a sample of the material that is suspected of containing a biological agent; (2) place the sample in an environment (such as a petrie dish with agar) in which certain biological agents, if present, can grow and multiply; and (3) after sufficient time has elapsed for any such agents to grow and replicate, visually identify (typically, with a microscope) the biological agent present in the nurturing environment.

Immuno-assay is another technique that is used to detect biological agents. In the immuno-assay technique, a sample of the material that is suspected of containing a biological agent is obtained and processed so as to place any biological agent present in the sampled material into a liquid suspension. The liquid with any biological agent suspended therein is then subjected to an immuno-assay test. In the test, an antibody that reacts with a specific biological agent (for example, *Bacillus anthracis*) is provided. If there is a biological agent present in the liquid sample and the agent is of the genus for which the antibody is present, a reaction will occur that is detectable. In one implementation, the liquid sample is applied to a glass microscope slide (also referred to as a "ticket") that includes antibodies for at least one biological agent. If a biological agent of the genus or species that corresponds to the antibody is present in the sampled liquid, there is a reaction between the antibody and the biological agent (antigent) that results in a visible indication of the presence of the biological agent being provided.

Another technique for detecting biological agents is the polymerase chain reaction (PCR) technique, which is a DNA analysis technique. In the PCR technique, the material that is suspected of containing a biological agent is sampled and, if necessary, transferred to a liquid medium. The DNA of any biological agent that is present in the sample is then placed in an environment that, for only a particular biological agent of interest, will cause a section or vectors of its DNA to multiply or replicate. For example, if the biological agent of interest is anthrax, the environment will only promote the multiplication of a vector of anthrax DNA, if any, present in the sample. If the particular biological agent of interest is present in the sample, the increase in the number of DNA for the biological agent produced by the noted environment creates a signal that can be detected by, for example, electrophoresis or fluorescence.

Yet another method for detecting biological agents is known as the MIDI technique. In the MIDI technique, the material that is suspected of containing a biological agent is sampled and, if needed, transferred to a liquid suspension. Any biological agent present in the liquid is then transferred to a nurturing environment, such as an agar filled petrie dish, so that the agent can grow and replicate. After any biological agent present in the sample has had sufficient time to grow and replicate, the agent is harvested from the nurturing environment and the fatty acids present within the cells of the agent are subjected to a process in which the fatty acids are converted to fatty acid methyl esters. The fatty acid methyl esters are then analyzed with a gas chromatograph to produce a "fingerprint" of the fatty acid methyl esters. The "fingerprint" of the unidentified agent is then compared to the "fingerprints" for known biological agents contained in a database (which commonly has 10,000 or more "fingerprints") to identify the biological agent in the sample. Due to the large number of "fingerprints" against which the unidentified "fingerprint" is compared, the technique identifies a number (typically, 10) of the known biological agents as having the closest "fingerprints" to the unidentified "fingerprint."

Yet a further technique for detecting biological agents is matrix assisted laser desorption ionization ("MALDI") mass spectrometry. As with the prior techniques, the material that is suspected of containing a biological agent is sampled and, if required, any biological agent present in the sample is transferred to a liquid suspension. The liquid containing any biological agent is then combined with an organic compound that is capable of absorbing infrared or ultraviolet light. The mixture is then dried so that any biological agent present in the sampled atmosphere is bound up in the crystalline matrix of the organic compound. The dried material is then bombarded with light from an infrared or ultraviolet laser that results in any protein associated with any biological agent present in the sample being ionized. The ionized proteins are then analyzed with a mass spectrometer to produce a mass spectrum that is compared to a data base of mass spectra of known proteins to identify the biological agent present in the sample.

SUMMARY OF THE INVENTION

The present invention provides a method for analyzing data related to the composition of an unidentified biological agent to both identify the agent and assess the reliability of the identification. In one embodiment, the method includes receiving the data related to the composition of the unidentified biological agent. Typically, the received data is type of mass spectral data (e.g., "full scan" MS, MS/MS, mix-Collision Induced Dissociation (CID) or full-CID) or chromatographic data. The received data is applied to a machine learning procedure that makes an initial identification of the unidentified biological agent. Depending upon the particular application of the method, the machine learning procedure may involve a single step or several steps. For instance, if the method is to be used to determine whether the unidentified biological agent is a bacteria, virus or toxin, it is feasible to implement the machine learning procedure in a single step. In contrast, if a detailed identification is required, such as a particular bacteria, the machine learning procedure is typically implemented in a multi-step fashion. The step or steps of the machine learning procedure are implemented using machine learning techniques, such as artificial neural networks and/or multi-variate statistical analysis. For example, in a multi-step machine learning procedure, each step utilizes a distinct artificial neural network.

Once the identification has been made, ion fragmentation analysis (e.g., MS/MS, mix-CID or full-CID) is used to assess the reliability of the identification provided by the machine learning procedure. In one embodiment, the ion fragmentation analysis is used to assess whether the initial identification of the unidentified biological agent is a false positive or a false negative. An example of a false positive would be if the unidentified biological agent is initially identified as a harmful virus and this identification is subsequently shown to be incorrect by the ion fragmentation analysis. In contrast, an example of a false negative would be if the unidentified biological agent is initially identified as one of the harmless forms of *E. coli* and is subsequently shown by the ion fragmentation analysis to be one of the harmful forms of *E. coli*. As the example demonstrates, in many cases, it is more important to detect a false negative (which means that a harmful biological agent is likely to be present) than a false positive (which means that a benign biological agent is likely to be present). In such a situation, the ion fragmentation analysis at least includes an assessment of whether the initial identification is a false negative. If the identification is confirmed by the ion fragmentation analysis, the identification is output.

A further embodiment of the invention provides a method for identifying an unidentified biological agent that makes use of a single set of data in the form of either a mix-CID or full-CD mass spectrum. The method includes receiving either the mix-CID or full-CID data on the unidentified biological agent The mix-CID data includes: (1) a portion of the data that would be obtained by subjecting a sample of the unidentified agent to a full scan mass spectrum analysis between high and low mass limits; and (2) a portion of the data that would be obtained by subjecting a series of multiple ions from a full-scan mass spectrum analysis to MS/MS analysis. The full-CD data includes: (1) all of the data that would be obtained by subjecting a sample of the unidentified agent to a full scan mass spectrum analysis between high and low mass limits; and (2) the data that would be obtained by subjecting all of the ions from a full scan mass spectrum analysis to MS/MS analysis. In one embodiment, the portion of the mix-CD or full-CID data that would be obtained from a full-scan MS analysis is used to make an initial identification of the unknown biological agent. The portion of the mix-CID or full-CID data that would be obtained by subjecting multiple ions from a full-scan mass spectrum analysis to MS/MS analysis is subsequently used to assess the reliability of the initial identification. Alternatively, the mix-CID or full-CD data is analyzed such that the identification and the reliability assessment are performed at the same time, rather than doing the initial identification and then the assessment. In one embodiment, artificial neural networks are used to evaluate both the MS data and the multiple ion MS/MS data (mix-CID or full-CID) at the same time. Other types of machine learning techniques, such as multi-variate statistical analysis, can also be used.

Another embodiment of the invention provides a method for rapid identification of an unidentified biological agent. The method includes receiving data on the biological compositional of the unidentified biological agent. In one embodiment, mass spectrum related data (e.g., MS data or CID data) is used. Alternatively, chromatographic data is used. The received data is subjected to an analysis step in which a decision is made as to whether the unidentified biological agent is, for example, in a first group of known agents or a second group of known agents. By determining that the unidentified agent is in either the first group or the second group, one entire group (the first or second) is eliminated from consideration. By repeating this style of analysis, a very detailed level of identification is attainable. For instance, if it is desirable to identify the unidentified biological agent at the specie or strain level (i.e., a very detailed level of identification), the identification technique may have several steps. If, however, a kingdom level identification (i.e., a low level of identification) is desired, it is possible to implement the analysis such that only one pass is needed to make the kingdom level identification. In one embodiment, the analysis is implemented with one or more artificial neural networks. Alternatively, a multi-variate statistical analysis or other machine learning technique is used. In any event, the method is faster, on average, than current analysis techniques that must potentially compare the "fingerprint" of the unidentified agent to all of the "fingerprints" of known agents in a library, many of which contain 10,000 or more "fingerprints."

DETAILED DESCRIPTION

Figure 1:
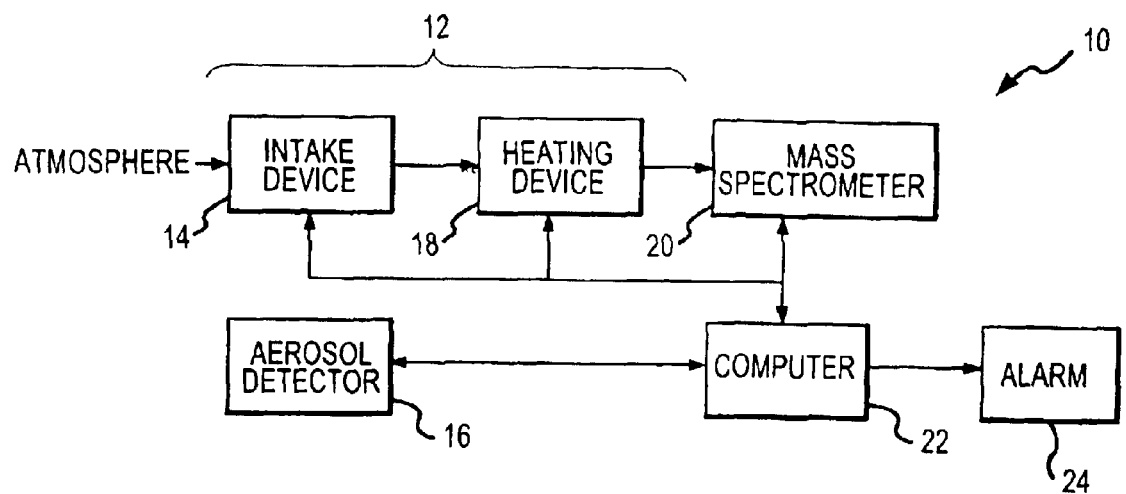
FIG. 1 is an example of a mass spectrum analyzer that is capable of sampling an atmosphere that may contain a bioaerosol and producing mass spectrum related data.

Before discussing the method for analyzing data related to an unidentified biological agent, one apparatus for sampling a biological agent and producing data relating to the composition of the biological agent is discussed. FIG. 1 illustrates one type of mass spectrometer analyzer 10 that is capable of sampling an atmosphere that may contain an unidentified biological agent (i.e., a bioaerosol) and analyzing the sample to provide data on the biological composition of a biological agent. The analyzer 10 includes a sampling section 12 for sampling the atmosphere. The sampling section 12 includes an intake device 14 for receiving the sample. In one embodiment, the intake device 14 is a virtual impactor that separates particles of a size in the range of a respirable particle (2 to 10 microns) from larger particles in the sample.

In some cases, it is desirable to operate the analyzer 10 only when an aerosol that may contain a bioaerosol is present. One such case is when the device is being powered by a stand-alone power source, such as a battery. In such cases, the sampling section 12 includes an aerosol detector 16 for detecting the presence of an aerosol in the atmosphere. If an aerosol is detected, the detector 16 causes a sample to be taken. Suitable detectors employ light scattering and laser technologies, as well as other technologies that are being used in smoke detectors and the like.

The sampling section 12 further includes a heating device 18 for distilling any lipids or volatile biomarkers from the sample of the atmosphere received by the intake device 14. A suitable heating device is a pyrolysis device that is commonly used in mass spectrometry. However, other devices capable of providing sufficient heat to distill out the lipids are also feasible, including laser based devices.

The device 10 further includes a mass spectrometer 20 for receiving the output of the heating device 18 and producing a mass spectrum of any unidentified biological material contained in the output of the heating device 18. Also included in the device 10 is a computer 22 that: (1) interfaces with the intake device 14, aerosol detector 16, heating device 18 and mass spectrometer 20; and (2) receives the mass spectrum output by the mass spectrometer 22. In the illustrated embodiment, the computer 22 is also capable of analyzing the mass spectrum to identify, as described hereinafter, unidentified biological materials in the sampled atmosphere and, if necessary, activating an alarm 24. It should, however, be appreciated that mass spectrum output by the mass spectrometer 20 can be conveyed to another computer (via a wire, wireless or combination wire and wireless system) to analyze the mass spectrum data if required or desired.

To prevent tampering, it is desirable that the analyzer 10 be located in a place that is not readily accessible. In this regard, it is particularly important that the intake device 14 be relatively inaccessible to prevent the inlet of the intake device 14 from being plugged. In addition, it is desirable that the intake device 14 be difficult to detect, especially if the intake device 14 cannot be located in an inaccessible location. A stand-alone power supply, such as a battery, is also desirable as either a back-up to a conventional power supply that is subject to sabotage or a primary power source.

Before discussing the method for analyzing data related to an unidentified biological agent, some of the different types of mass spectrometer (MS) data that can be analyzed are briefly described. One way to distinguish different types of MS data is the scan mode used to obtain the data. "Full-scan" mode mass spectrometer data is obtained by subjecting the material of interest to a mass spectrometer that is set to make a "full-scan" between two mass limits, a low mass limit and a high mass limit.

Tandem MS or MS/MS mode mass spectrometer data is obtained by initially isolating ions of a single mass from the material of interest using a mass spectrometer. These ions are then subjected to high energy collisions with an inert gas to induce ion fragmentation. The collision induced dissociation (CID) fragments the ions into smaller fragment or product ions that have unique intensities and masses relative to the parent ion. Finally, the fragment ions are subjected to a "full-scan" MS analysis. The MS/MS technique can be implemented in a linear quadrupole mass spectrometer or quadrupole ion trap mass spectrometer.

Mix-CD data is obtained by substantially simultaneously isolating multiple ions of different masses for the material of interest using a mass spectrometer. After the ions have been isolated, the ions are subjected to simultaneous CID to produce fragment ions for each of the multiple, parent ions. The fragment ions are then subjected to a "full-scan" MS analysis. The resulting spectrum includes a portion of the data that would be obtained from a full-scan MS analysis and the MS/MS data for several ions of different masses. A quadrupole ion trap mass spectrometer is used to obtain mix-CID data.

Full-CD data is obtain by substantially simultaneously subjecting all of the ions between a low mass limit and a high mass limit to CID to produce fragment ions for each of the parent ions. The fragment ions are then subjected to a full-scan MS analysis between the mass limits. In this case, the resulting mass spectrum includes all of the data that would be obtained for a full-scan MS analysis between the mass limits and all of the data for the fragment ions between the mass limits. A quadrupole ion trap mass spectrometer is used to obtain full-CID data.

With reference to FIGS. 2A–2H, a method for analyzing data relating to the composition of an unidentified biological agent is described. The analysis is performed by a computer that includes a processor, memory for storing the program that implements the methodology and any data required by the program, and appropriate input/output devices. Initially, data associated with the composition of an unidentified biological agent is received by the computer. The data is either mass spectrum or chromatographic data. Potential sources of mass spectrum data are mass spectrometers with either electron ionization (EI) or chemical ionization (CI) devices, and the MALDI system. Typically, chromatographic data is provided by a gas chromatograph. However, other sources of chromatographic data are also feasible. For purposes of the following description of the analysis method, however, the source of the data is a mass spectrometer.

After the mass spectrum data has been received, the method involves rapidly analyzing the received mass spectrum data to provide an initial identification of the unidentified biological agent. Generally, the initial identification involves the use of machine learning techniques, such as artificial neural networks (ANNs) and/or multi-variate statistical analysis, to make the initial identification. In the described embodiment, artificial neural networks are utilized. Generally, the artificial neural networks utilized in making the initial identification of the unidentified biological agent are trained with the mass spectra of known biological agents. The artificial neural networks can also be trained with possible background and interference mass spectra (e.g., pollen, fungi, and vehicle emissions). In operation, an ANN receives the mass spectrum data and decides, based upon the prior training, whether the mass spectrum is more likely than not (i.e., the numerical output of the ANN has a value greater than 0.5 on a scale extending from 0 to 1) to be associated with one of at least two "targets." By defining the "targets" to be groups of biological agents, ANNs facilitate rapid identification of the unknown biological agent with which the received mass spectrum is associated. For instance, the ANN-1 in FIG. 2A operates to decide whether the received mass spectrum data is more likely than not to be one of six possible targets, five groups of biological agents and one group of chemical agents. Specifically, the five biological targets are bacteria, toxins, viruses, pollen and fungi. Consequently, the operation of ANN-1 serves to quickly reduce the number of possible biological agents from several different general types of biological agents to a single general type of biological agent.

The ANN-1 operates by looking for specific biomarkers within the mass spectrum of the unidentified biological agent that are associated with each of the general types of biological agents. To elaborate, if the ANN-1 identifies biomarkers in the mass spectrum indicative of the presence of lipid, protein and nucleic acid biomarkers in the unidentified agent, the ANN-1 concludes that the unidentified biological agent is more likely than not a bacteria. Similarly, the detection of a cholesterol biomarker by ANN-1 leads to the conclusion that the unidentified biological material is most likely to be a virus. If only a protein biomarker is identified by the ANN-1, then the ANN-1 concludes that the unidentified biological agent is most likely to be a toxin. The presence of a sterol and polyunsaturated acids lead the ANN-1 to conclude that the unidentified agent is most likely a fungi. The presence of a specific fatty acid composition causes the ANN-1 to decide that the unidentified agent is more likely than not a pollen. Finally, if none of the previously noted biomarkers are present, the ANN-1 concludes that the unidentified agent is not a biological agent but possibly a chemical agent. The specific chemical agent is identified by comparing the mass spectrum to a library of spectra for known chemical agents.

FIGS. 2B–2E illustrate four possible ways to obtain a more specific initial identification of the bacteria associated with the received mass spectrum. One difference between each of the four possible ways is that different numbers of ANNs are used to reach an initial identification of the specific bacteria with which the mass spectra is associated. One benefit of using more ANNs is that each ANN is trained to make a simple decision based upon a specific criteria (e.g., such as a Gram positive/negative criteria) and the subsequent ANNs to a particular ANN make simple decisions that increase in specificity. As a consequence, the ultimate identification is more reliable than when fewer ANNs, which must make more complex decisions based on more criteria, are utilized.

Figure 2A:
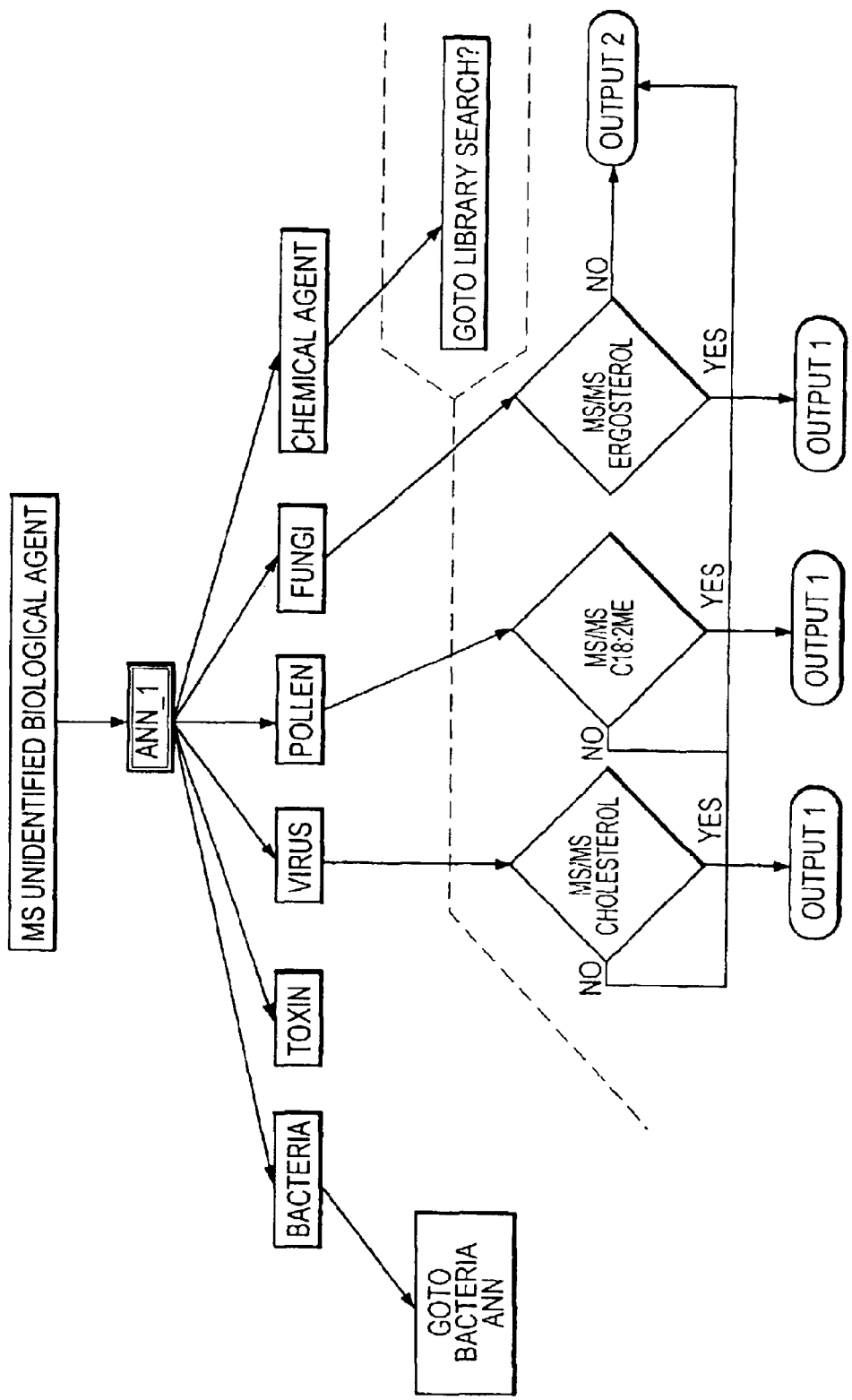
FIGS. 2A–2H illustrate one embodiment of a method for analyzing data, such as the mass spectrum data produced by the MS analyzer shown in FIG. 1, to identify and unidentified biological agent.
Figure 2B:
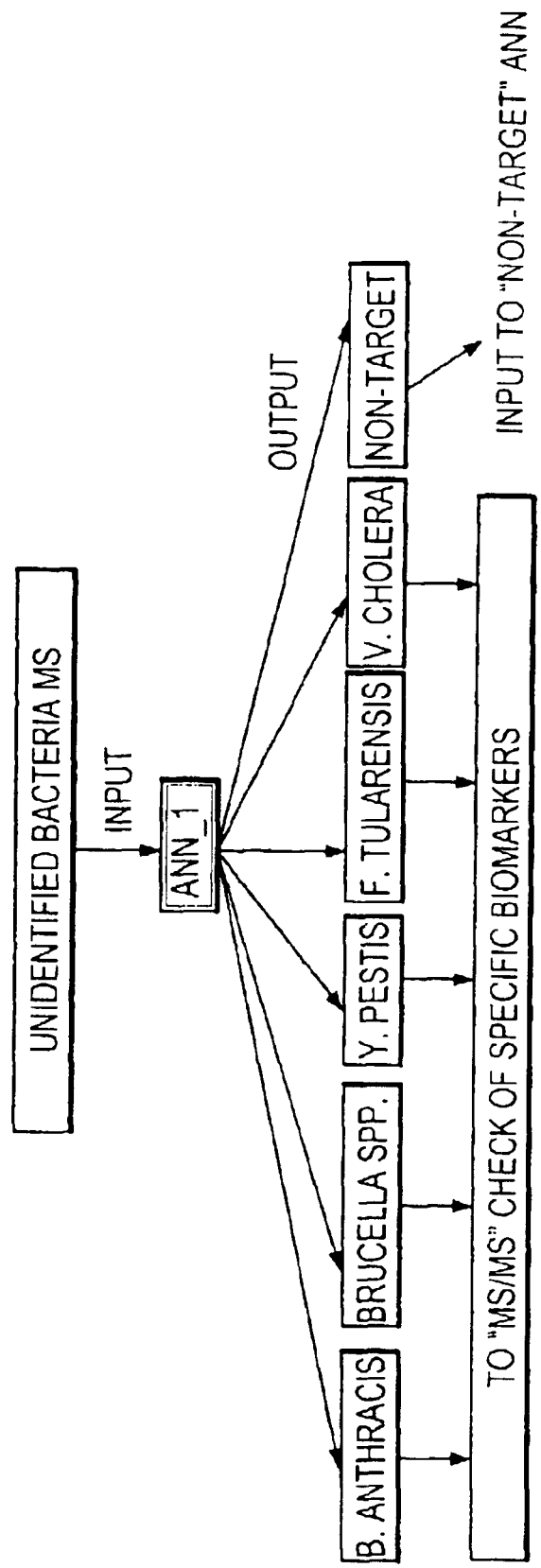

In FIG. 2B, the mass spectrum for the unidentified bacteria is applied to ANN-1, which has been trained to identify a unique group of "target" bacteria: *B. anthracis, Brucella spp., Y. pestis, F. tularensis* and *V. cholera*. It should be appreciated that an ANN can be trained to identify any desired number of different bacteria. Based upon the mass spectrum, the ANN-1 identifies either: (1) one of the five target bacteria as the bacteria associated with the received mass spectrum or (2) none of the five target bacteria as the bacteria associated with the received mass spectrum, i.e., a "non-target" bacteria. Typically, the "non-target" bacteria represents a large group of harmless bacteria. Consequently, the ANN-1 operates to rapidly identify the bacteria associated with the received mass spectrum. If ANN-1 makes an initial identification that the unidentified bacterial agent is a "non-target" bacteria, the mass spectrum is applied to a "non-target" ANN, which is described with respect to FIGS. 2G and 2H, to determine if the initial identification is a false negative.

Figure 2C:
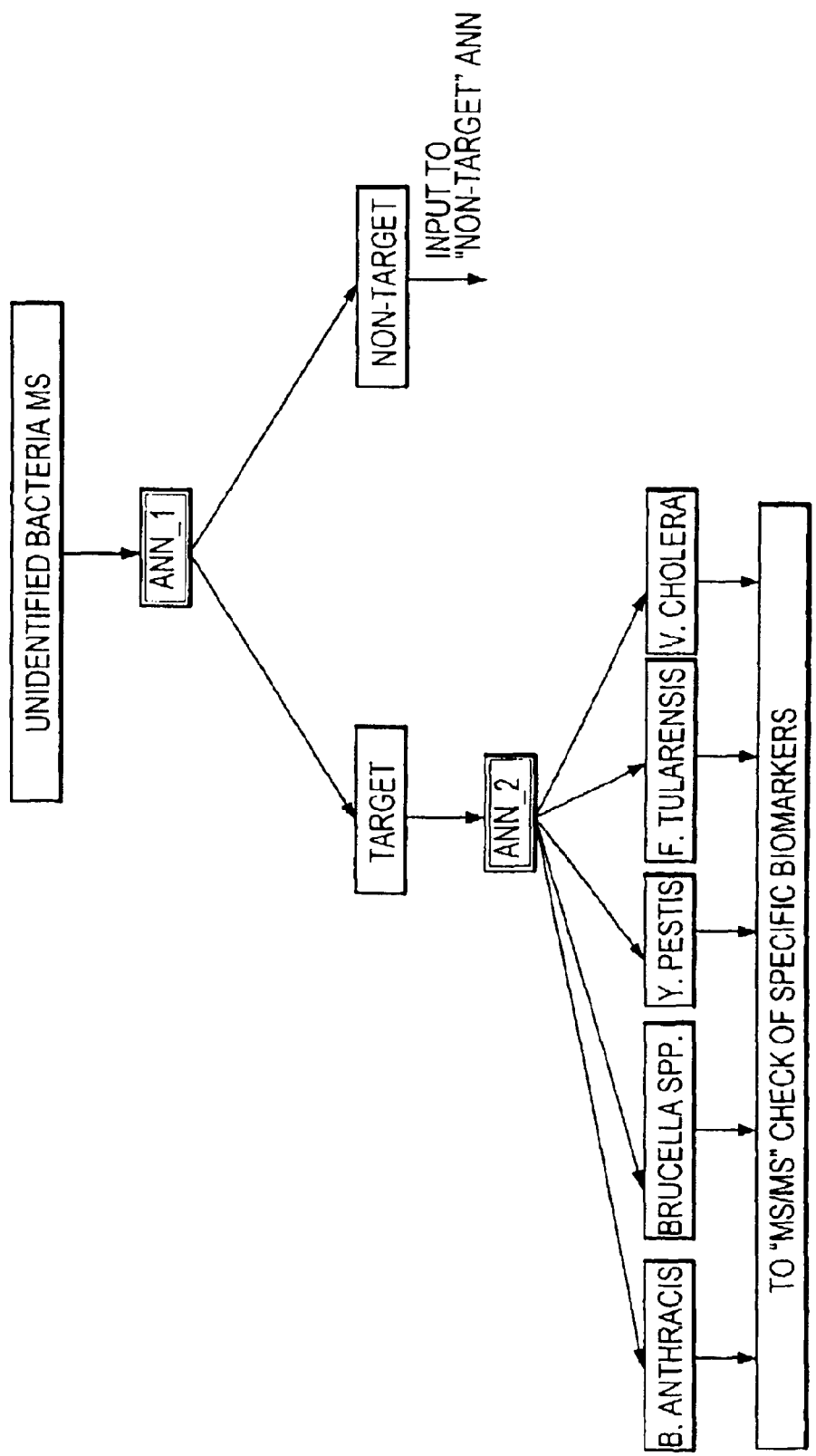

In FIG. 2C, two ANNs are utilized to make the initial identification of the bacteria associated with the received mass spectrum. The ANN-1 is trained to decide whether the received mass spectrum is more likely that not to be associated with: (I) the group of five "target" bacteria, or (2) a group of "non-target" bacteria if the ANN-1 concludes that the received mass spectrum is most likely associated with the group of five "target" bacteria, the mass spectrum is applied to ANN-2. The ANN-2 is trained to decide, based on the received mass spectrum, which one of the five possible "target" bacteria is most likely to be present. If ANN-1 makes an initial identification that the unidentified bacterial agent is a "non-target" bacteria, the mass spectrum is applied to a "non-target" ANN, which is described with respect to FIGS. 2G and 2H, to determine if the initial identification is a false negative.

Figure 2D:
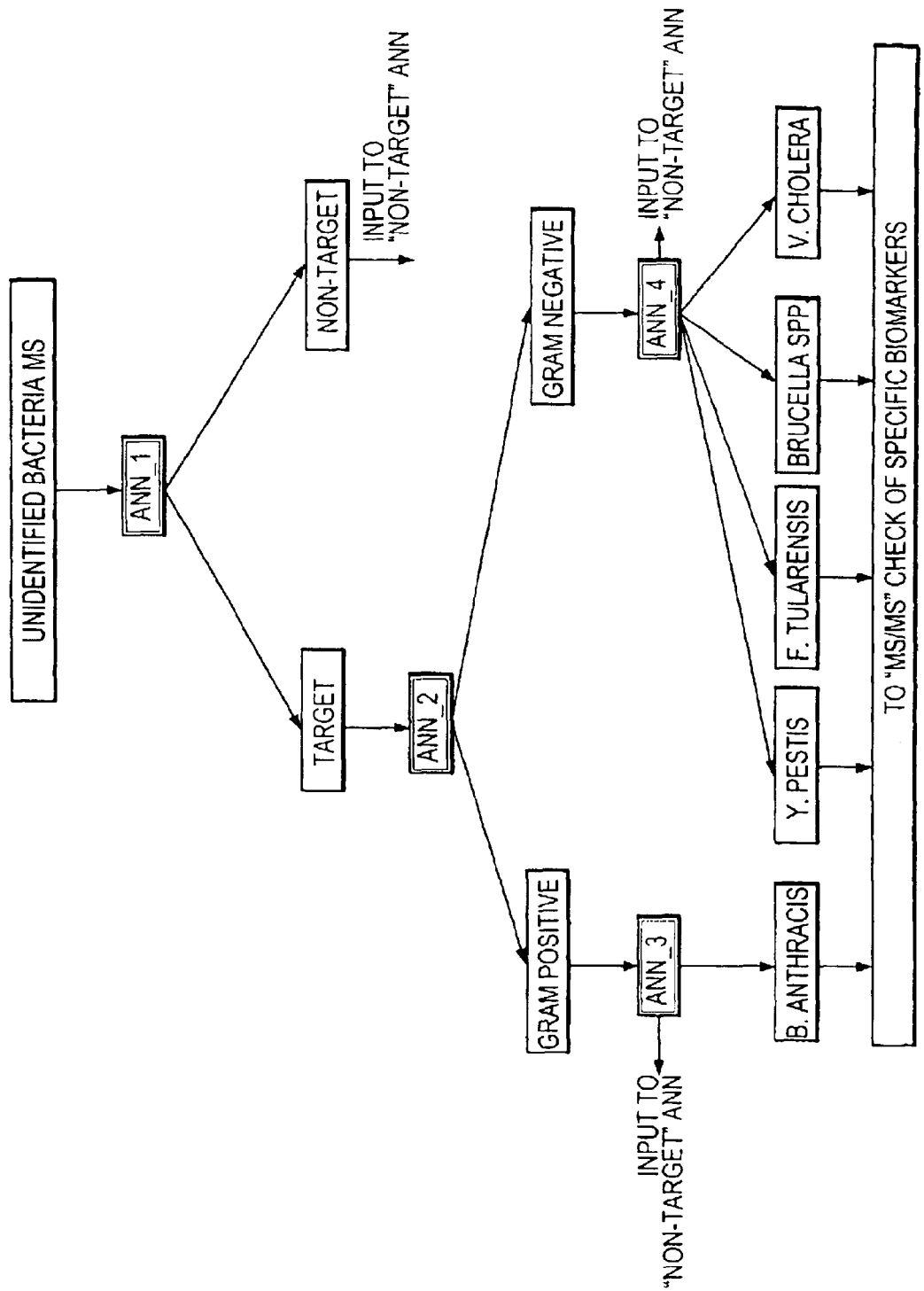

In FIG. 2D, up to three ANNs are utilized to make the initial identification of the bacteria most likely to be associated with the received mass spectrum. The ANN-1 is trained to decide whether the received mass spectrum is most likely to be associated with the group of five "target" bacteria or a group of "non-targeted" bacteria. If the received mass spectrum is likely to be characteristic of one of the five "target" bacteria, the mass spectrum is applied to ANN-2 to determine whether the mass spectrum is indicative of a Gram-positive or Gram-negative type of bacteria. If the received mass spectrum is indicative of a Gram positive bacteria, the ANN-2 concludes that the unidentified biological agent is likely to be *B. anthracis*. To confirm this conclusion, the mass spectrum is applied to ANN-3, which concludes that the received mass spectrum is indicative of *B. anthracis* only if there is substantial certainty thereof, i.e., a probability approaching ion a probability scale extending from 0 to 1. If this high degree of certainty is not present, the mass spectrum is applied to a "non-target" ANN, which is described with respect to FIGS. 2G and 2H. On the other hand, if the ANN-2 concludes that the received mass spectrum is indicative of a Gram negative bacteria, the unidentified agent is likely to be one of the other four "target" bacteria. To determine which one of the four "target" bacteria, the mass spectrum is applied to ANN-4. If ANN-4 makes an initial identification that the unidentified bacterial agent is a "non-target" bacteria, the mass spectrum is applied to a "non-target" ANN, which is described with respect to FIGS. 2G and 2H, to determine if the initial identification is a false negative.

Figure 2E:
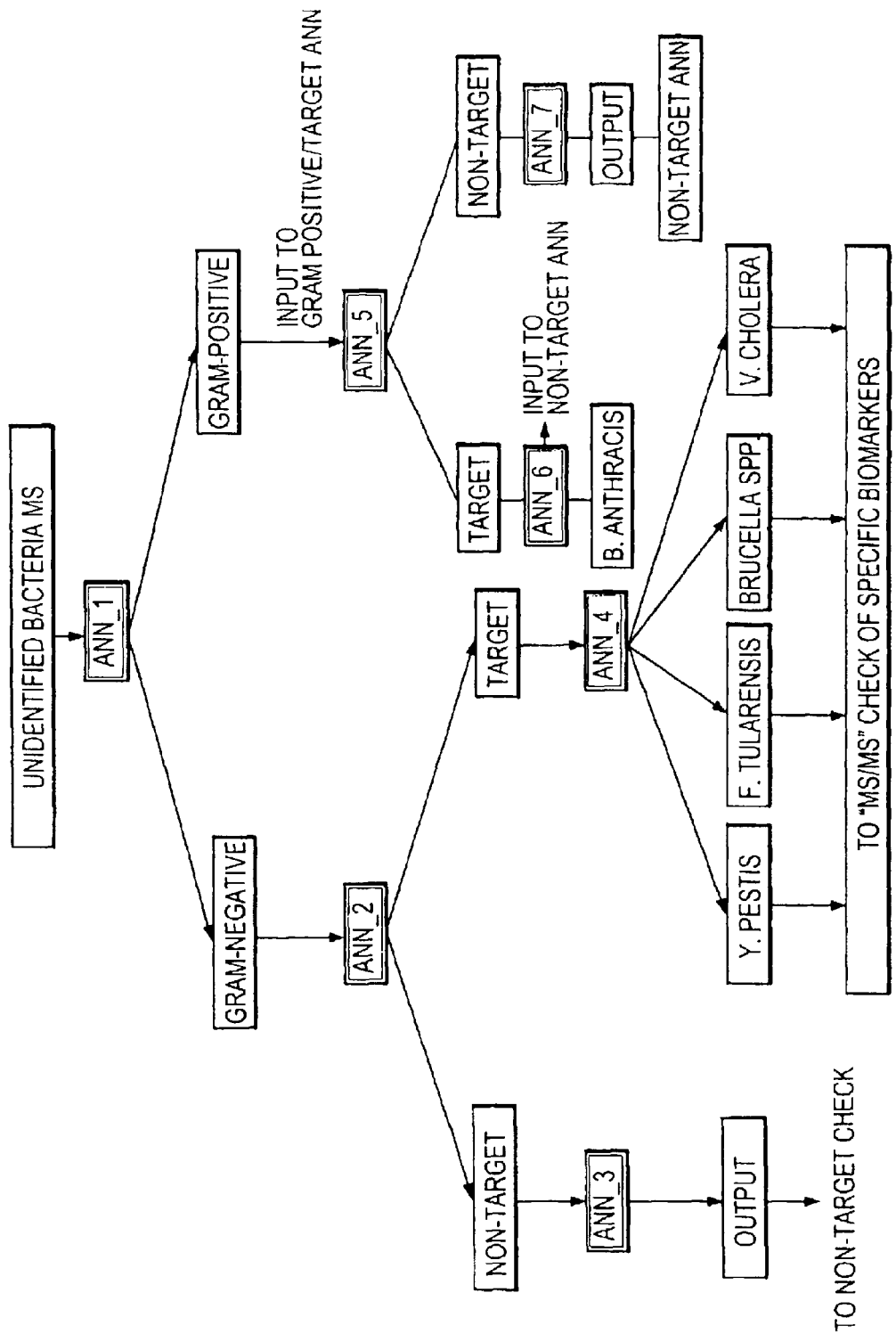

In FIG. 2E, the received mass spectrum is initially applied to ANN-1 to assess whether the unidentified bacteria is a Gram positive or Gram negative bacteria. If ANN-1 concludes that the mass spectrum is more likely than not associated with a Gram negative bacteria, the mass spectrum is applied to ANN-2. The ANN-2 determines whether the received spectrum is more likely than not associated with one of the bacteria in the group four "target" bacteria of *Y. pestis, F. tularensis, Brucella spp.* and *V. cholera*, or a "non-target" group of Gram-negative bacteria. To confirm the "non-target" Gram-negative identification, the mass spectrum is applied to ANN-3, which concludes that the received mass spectrum is indicative of one of a plurality of "non-target," Gram-negative bacteria only if there is substantial certainty thereof, i.e., a probability approaching Ion a probability scale extending from 0 to 1. If there is substantial certainty, the identity of the "non-target," Gram-negative bacteria is output. If, however, ANN-2 determines that the received mass spectrum is most likely to be characteristic of one of the four "target" bacteria the mass spectrum is applied to ANN-4 for a final determination.

With continuing reference to FIG. 2E, if ANN-1 determines the mass spectrum to be most likely associated with a Gram positive bacteria (e.g., *B. anthracis*), the mass spectrum is applied to ANN-5 to determine whether a "target" or "non-target," Gram-positive bacteria is represented by the mass spectrum. If the received mass spectrum is indicative of a "target" Gram-positive bacteria, the ANN-5 concludes that the unidentified biological agent is likely to be *B. anthracis*. To confirm this conclusion, the mass spectrum is applied to ANN-6, which concludes that the received mass spectrum is indicative of *B. anthracis* only if there is substantial certainty thereof, i.e., a probability approaching 1 on a probability scale extending from 0 to 1. If this high degree of certainty is not present, the mass spectrum is applied to a "non-target" ANN, which is described with respect to FIGS. 2G and 2H. If, however, the received spectrum is indicative of a "non-target" Gram-positive bacteria, the mass spectrum is applied to the ANN-7. The ANN-7 concludes that the received mass spectrum is indicative of one of a plurality of "non-target," Gram-positive bacteria only if there is substantial certainty thereof, i.e. a probability approaching on a probability scale extending from 0 to 1. If this high degree of certainty is present, the mass spectrum is applied to a "non-target" ANN, which is described with respect to FIGS. 2G and 2H, to determine if the initial identification is a false negative.

FIGS. 2B–2E illustrate four possible procedures that use machine learning devices, such as ANNs, to rapidly analyze mass spectral data to make an initial determination as to whether the mass spectrum is associated with five specific "target" bacteria that present substantial health risks or with "non-target" bacteria. It should be appreciated that other procedures that use machine learning devices, such as ANNs, to make an initial identification of the noted "target" or "non-target" bacteria based upon biomarkers are feasible. Further, it should be appreciated that the method can be altered to make a rapid initial identification of other "target" bacteria and "non-target" bacteria. As a consequence, the specific biomarkers used by the ANN or other machine learning device are also likely to be altered. For example, the use of Gram positive/negative biomarkers may not be appropriate when the "target" bacteria do not include B. anthracis. Further, although not shown, the method of rapidly identifying biological agents by using machine learning devices to eliminate groups of possible biological agents based on biomarkers is also applicable to a more specific initial identification of toxins, viruses, pollen and fungi.

It should also be appreciated that the initial identification of an unidentified biological agent takes less than one minute, and more preferably less than one second. While these times for an initial identification have been determined for initial identification techniques that utilize up to three machine learning techniques (e.g., ANNs) to make the initial identification, it is believed that these times are also applicable for initial identification techniques that utilize up to ten machine learning techniques to make an initial identification. Presently, the use of ten machine learning procedures in an initial identification is considered to be the maximum foreseeable number of machine learning techniques that would be used to make an initial identification. However, it is believed that the time needed to make an initial identification is relatively insensitive to the number of machine learning techniques utilized to make the identification. Consequently, it is believed that the noted times are also achievable when greater numbers machine learning procedures are utilized to make the initial identification.

Once the initial identification has been made, the method proceeds to test the reliability of the initial identification. To elaborate, the initial identification is subject to error. There are two types of errors possible, false positives and false negatives. A false positive occurs when the received mass spectrum is initially identified as being associated with one of the "target" biological agents and this identification is incorrect. In the illustrated example, a false positive would occur if the received mass spectrum is initially identified as being associated with one of the "target" biological agents when it is not associated with one of these agents (e.g., the soil bacterium Pseudomonas being identified as Y. pestis). In most cases, the "target" biological agents will be those agents that present substantial health risks. In this case, if the initial identification is incorrect, an alarm may be needlessly raised.

A false negative occurs when the received mass spectrum is initially identified as being in the "non-target" group and this identification is incorrect, i.e., the mass spectrum is associated with a "target" biological agent. In the situation where the "target" biological agents are those agents that present substantial health risks, a false negative will result in an alarm not being raised when an alarm should be raised.

To address the potential for a false positive, the reliability of an initial identification as being one of the "target" biological agents is tested using ion fragmentation analysis. With reference to FIGS. 2A–2E, the ion fragmentation analysis utilized is MS/MS analysis, which operates upon the mass spectrum (MS) associated with the fragmentation of a specific ion in the mass spectrum (MS) data, hence the term MS/MS. Sources of data from which MS/MS data can be produced include mass spectrometers, electro-spray ionization devices and the MALDI system. In most cases, time constraints will require that the MS/MS data be produced from a second sample of the material that is suspected of containing a biological agent. Consequently, the MS/MS data are received separately from and after the MS data used to make the initial identification. It is also feasible to produce MS/MS data based upon the output of a gas chromatograph, i.e., a GC-MS/MS system.

With reference to FIG. 2A, the false positive testing for virus, pollens and fungi is described. If the received mass spectrum was initially identified as a "target" virus, the MS/MS analysis is performed on cholesterol. If the MS/MS mass spectrum for cholesterol is present, the initial identification of a virus is confirmed and output. If the MS/MS mass spectrum for cholesterol is not present, the initial identification is disaffirmed, i.e., a false positive has been identified, processing ceases, and an output is provided that the received mass spectrum is unidentifiable. Similarly, if a pollen was initially identified, the MS/MS analysis confirms or disaffirms the initial identification based upon the presence or absence of the MS/MS mass spectrum for the C18:2ME biomarker. With respect to an initial identification of a fungi, the MS/MS analysis confirms or disaffirms the initial identification based upon the presence or absence of the MS/MS mass spectrum for the ergosterol.

Figure 2F:
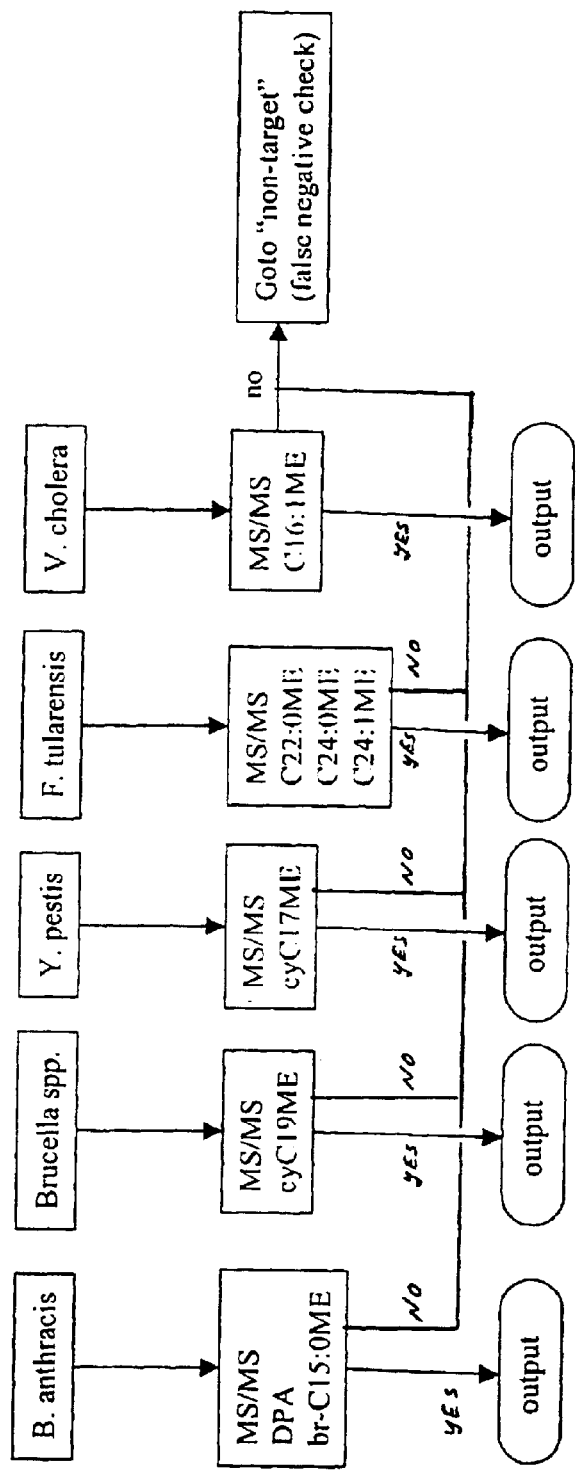

FIG. 2F illustrates the false positive testing when the initial identification made by one of the machine learning related procedures shown in FIGS. 2B–2E has identified one of the five "target" bacteria. With respect to the initial identification of B. anthracis, the presence or absence of the mass spectra in the MS/MS data for dipicolinic acid and br-C15:0ME confirms or disaffirms the initial identification of B. anthracis. Likewise, the presence or absence of the mass spectrum for cyC19ME in the MS/MS data confirms or disaffirms the initial identification of Brucella ssp; the presence/absence of the mass spectrum for cyC17ME in the MS/MS data confirms/disaffirms the initial identification of Y. pestis; the presence/absence of the mass spectra for C22:0ME, C24:0ME and C24:1ME confirms/disaffirms the initial identification for F. tularensis; and the presence/absence of the mass spectrum for C16:1ME in the MS/MS data confirms/disaffirms the initial identification of V. cholera.

It should be appreciated that if the method for making an initial identification is applied to different "target" bacteria and "non-target" bacteria, the biomarkers used to identify a false positive are likely to change. For instance, if E. coli is the desired target microorganism and is initially identified, the biomarkers used to confirm or disaffirm this identification will be different than those for the five "target" bacteria shown in FIG. 2F.

Figure 2G:
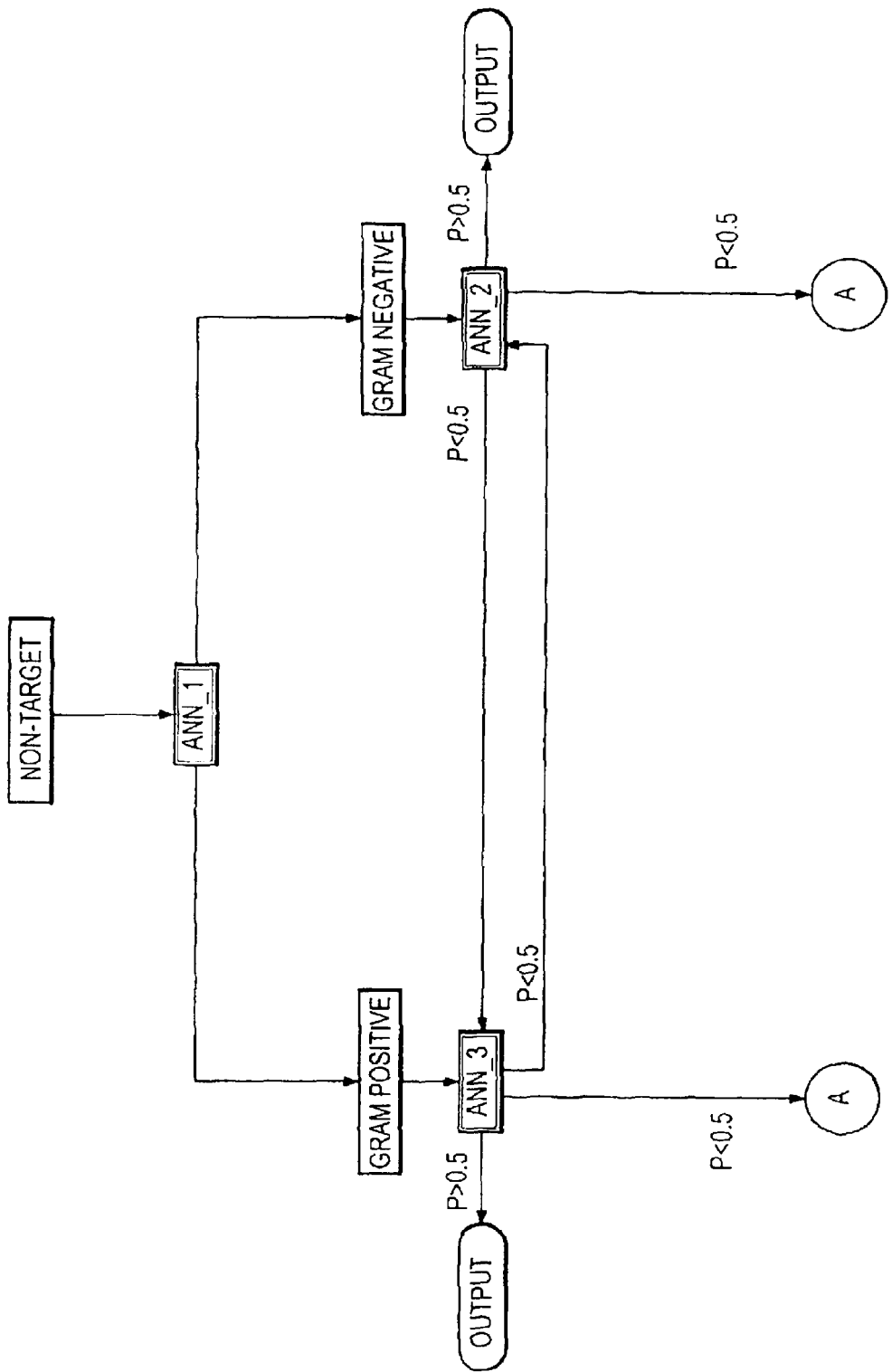
Figure 2H:
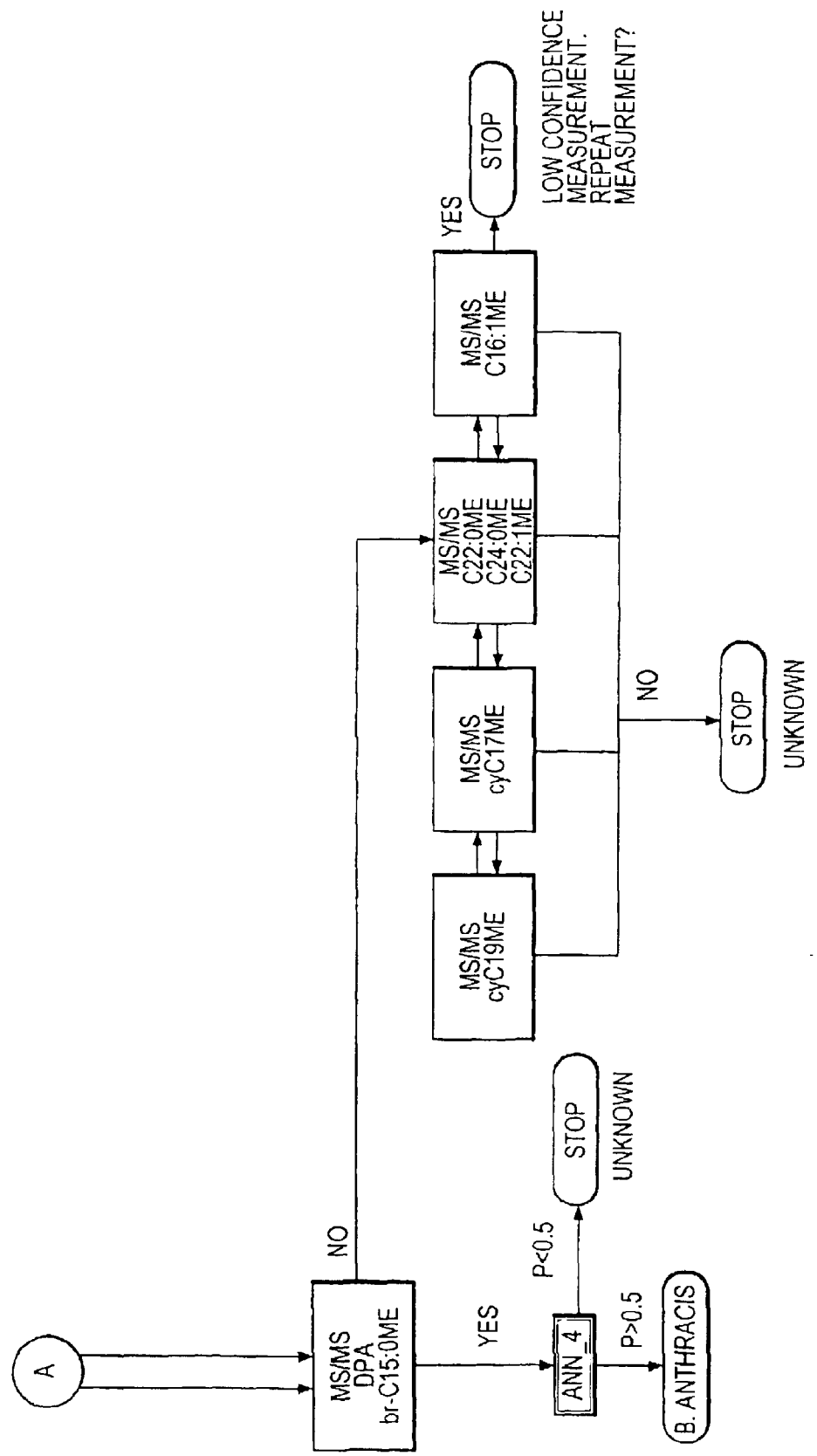
Figure 2F:
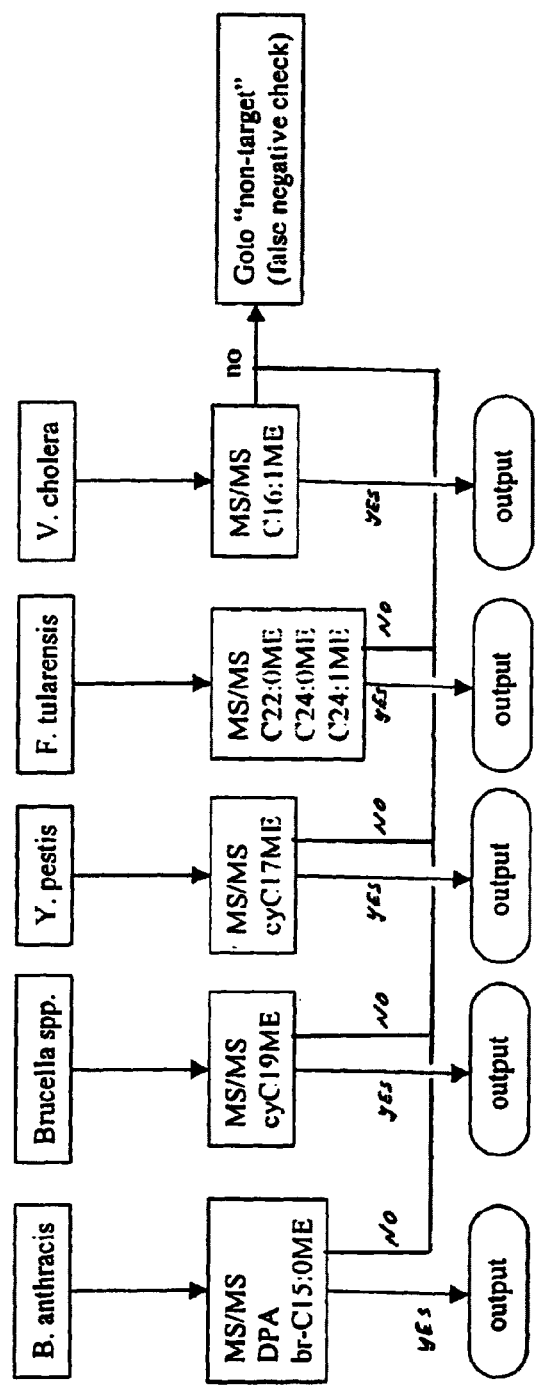

To address the potential for a false negative, the reliability of an initial identification as being one of the "non-target" biological agents is tested to determine if the received mass spectrum is associated with one of the "target" biological agents. FIGS. 2G and 2H illustrate the false negative test for the case in which the initial identification identified the received mass spectrum as being associated with a "non- "target" bacteria, i.e., a bacteria other than the five "target" bacteria shown in FIGS. 2B–2E. Initially, the originally received mass spectrum (not the MS/MS spectrum) is applied to ANN-1 to assess whether the mass spectrum is more likely than not representative of a Gram-positive or Gram-negative bacteria. If ANN-1 determines that the mass spectrum is most likely to be representative of a Gram-negative bacteria, the received mass spectrum is applied to the ANN-2. The ANN-2 determines whether the conclusion that the received mass spectrum is representative of a "non-target" Grain-negative bacteria is more likely than not to be correct. If ANN-2 determines that the conclusion is more likely than not to be correct (i.e., the probability (P) is greater than 0.5), the conclusion that the received mass spectrum is associated with a "non-target," Gram-negative bacteria is output to the user. If, however, ANN-2 determines that the conclusion is likely to be in error (P<0.5, which means that the bacteria may be a Gram-positive bacteria), the mass spectrum is applied to the ANN-3. The ANN-3 determines whether the new conclusion that the received mass spectrum is representative of a "non-target" Gram-positive bacteria is likely to be correct. If the ANN-3 determines that the new conclusion is likely to be correct (P>0.5), the conclusion that the received mass spectrum is a "non-target" Gram-positive bacteria is output to the user. If, however, the ANN-3 determines that the conclusion is incorrect (i.e., the mass spectrum is not representative of a "non-target," Gram-positive or Gram-negative bacteria) further processing is required to make a determination of whether the received mass spectrum is representative of one of the "target" bacteria or an unknown bacteria, as shown in FIG. 2H.

With continuing reference to FIG. 2G, the analysis is described if ANN-1 concludes that the received mass spectrum is likely to be representative of a "non-target" Gram-positive bacteria. If ANN-1 reaches this conclusion, the received mass spectrum is applied to ANN-3. The ANN-3 determines whether the conclusion that the received mass spectrum is representative of a "non-target" Gram-positive bacteria is more likely than not to be correct. If ANN-3 determines that the conclusion is more likely than not to be correct (i.e., the probability (P) is greater than 0.5), the conclusion that the received spectrum is associated with a "non-target," Gram-positive bacteria is output to the user. If, however, ANN-3 determines that the conclusion is likely to be in error (P<0.5, which means that the bacteria may be a Gram-negative bacteria), the mass spectrum is applied to the ANN-2. The ANN-2 determines whether the new conclusion that the received mass spectrum is representative of a "non-target," Gram-negative bacteria is likely to be correct. If the ANN-2 determines that the new conclusion is likely to be correct (P>0.5), the conclusion that the received mass spectrum is a "non-target," Gram-negative bacteria is output to the user. If, however, the ANN-2 determines that the conclusion is incorrect (i.e., the mass spectrum is not representative of a "non-target" Gram-positive or Gram-negative bacteria) further processing is required to make a determination of whether the received mass spectrum is representative of one of the "target" bacteria or an unknown bacteria, as shown in FIG. 2H.

FIG. 2H illustrates the further false negative analysis that is performed if the analysis of the received mass spectrum, which is shown in FIG. 2G, reaches a conclusion that the received mass spectrum is not representative of a "non-target," Gram-positive or Gram-negative bacteria. Stated differently, the prior false negative analysis has concluded that the received mass spectrum is representative of either a "target" bacteria or an unknown bacteria (i.e., a bacteria that the ANNs have not been trained to recognize). The further false negative analysis begins with determining whether the mass spectrum for dipicolinic acid and br-C15:0ME are present in the MS/MS data. If both dipicolinic acid and brC15:0ME are present than it is likely the received mass spectrum is representative of B. anthracis. To confirm this conclusion the received mass spectrum is applied to ANN-4. If ANN-4 concludes that the received mass spectrum is likely to be representative of *B. anthracis*, this conclusion is output to the user. If, on the other hand, ANN-4 concludes that this conclusion is in error, the conclusion that the received mass spectrum is associated with an unknown bacteria is output to the user.

With continuing reference to FIG. 2H, if the MS/MS analysis of the received mass spectrum does not find the mass spectra for dipicolinic acid and br-C15:0ME, the MS/MS data is analyzed to determine if the biomarkers associated with one of the four "target" bacteria other than *B. anthracis* are present. The biomarkers associated with these four bacteria were previously described with respect to FIG. 2F. If none of the biomarkers associated with the four "target" bacteria are present, the conclusion that the received mass spectrum is associated with an unknown bacteria is output to the user. If, however, the biomarker or biomarkers representative of one of the four bacteria are present, the identified "target" bacteria is output to the user with a note that the identification is subject to uncertainty and a recommendation that the test be repeated.

It should be appreciated that if the initial identification process is applied to different "target" and "non-target" bacteria, the false negative test is likely to change. Further, although not shown, the false negative analysis is capable of being adapted to situations in which the initial identification involves "non-target" toxins, viruses, pollens and fungi.

One possible modification to the method is to analyze mix-CID or full-CID data rather than MS data (or chromatographic data) and MS/MS data. As previously noted, mix-CID data is produced by a mass spectrometer and contains at least a portion of the data that would be obtained from a full-scan MS analysis and MS/MS data for fragment ions of a number of parent ions of different masses. Full-CID data contains all of the data that would be obtained from a full-scan MS analysis between two mass limits and all of the data for the fragment ions between-two mass limits. One advantage of using either mix-CID or full-CID data is that only one sample of the material that is suspected of containing a biological agent needs to be taken and only one analysis performed. In contrast, when MS or chromatographic data and MS/MS data are used, timing constraints frequently require that two samples of the material suspected of containing the unidentified biological agent be taken and two analyses performed. In the first analysis, the first sample is used to produce the MS data that is used in making the initial identification, and the second sample is used to test the reliability of the initial identification. One way to use the mix-CID data or full-CID data is to use the MS portion of the data to make the initial identification. The MS and/or MS/MS portion of the CID data are then used, if needed, in performing a reliability analysis as previously described.

Another way to use the mix-CID data or full-CID data is to adapt the machine learning procedures (e.g., ANNs) to use both the MS portion and MS/MS portion of the data in the identification phase. By adapting the machine learning procedure in this manner a highly reliable identification of the unidentified biological agent is obtained that potentially eliminates the need for a reliability phase.

It should be appreciated that: (1) mass spectrum related data can be applied to several ANNs to obtain decisions from each of the ANNs and then the decisions can be analyzed to reach a conclusion; or (2) mass spectrum related data can be applied to one ANN to obtain a decision from the ANN and then the decision can be used to determine which ANN the mass spectrum related data is to be applied to next; or (3) a combination of these approaches can be used.

The foregoing description of the invention has been presented for purposes of illustration and description. Further, the description is not intended to limit the invention to the form disclosed herein. Consequently, variations and modification commensurate with the above teachings, and the skill or knowledge in the relevant art are within the scope of the present invention. The embodiment described hereinabove is further intended to explain the best mode known of practicing the invention and to enable others skilled in the art to utilize the invention in various embodiments and with the various modifications required by their particular applications or uses of the invention. It is intended that the appended claims be construed to include alternate embodiments to the extent permitted by the prior art.

What is claimed is:

1. A method for analyzing data related to an unidentified biological agent to identify the unidentified biological agent, the method comprising:
   receiving data on the biological composition of the unidentified biological agent contained in a sampled material; and
   first analyzing said data with a machine learning procedure to eliminate at least one group of known biological agents from at least two different groups of known biological agents that may include the unidentified biological agent, wherein at least one of said at least two different groups of known biological agents includes a plurality of sub-groups of biological agents; and
   second analyzing, following said first analyzing step, said data with a different machine learning procedure relative to the machine learning procedure utilized in the first analyzing step, wherein said different machine learning procedure is chosen based upon the elimination of said at least one group of known biological agent in said first analyzing step and provides a more refined identification of the unidentified biological agent than the machine learning procedure utilized in the first analyzing step.

2. A method, as claimed in claim 1, wherein:
   said step of receiving includes receiving data on the biological composition of the unidentified biological agent, where the unidentified biological agent is in the form of a bioaerosol.

3. A method, as claimed in claim 1, wherein:
   said step of receiving includes receiving mass spectrum data on the unidentified biological agent.

4. A method, as claimed in claim 1, wherein:
   one of said machine learning procedure and said different machine learning procedure includes a neural network.

5. A method, as claimed in claim 1, wherein:
   one of said machine learning procedure and said different machine learning procedure includes multi-variate statistical analysis.

6. A method, as claimed in claim 1, wherein:
   said at least two different groups of biological agents includes at least two of the following: bacteria, viruses, toxins, pollens and fungi.

7. A method, as claimed in claim 1, wherein:
   said at least two different groups of biological agents includes a first group of bacteria and a second group of bacteria.

8. A method, as claimed in claim 1, further comprising:
   receiving further data on the biological composition of the unidentified biological agent contained in a sampled material; and
   using said further data to assess the possibility that said initial identification is incorrect.

9. A method, as claimed in claim 8, wherein:
   said step of receiving further data includes receiving MS/MS data on the unidentified biological agent.

10. A method, as claimed in claim 1, wherein:
    said step of receiving includes receiving collision induced dissociation data on the unidentified biological agent, wherein said collision induced dissociation data includes at least some of the data that would be obtained from an MS analysis of the unidentified biological agent and at least some of the data that would be obtained from an MS/MS analysis of the unidentified biological agent.

11. A method, as claimed in claim 1, wherein:
    said machine learning procedure and said different machine learning procedure are each a multi-variate statistic analysis.

12. A method, as claimed in claim 1, wherein:
    said machine learning procedure and said different machine learning procedure are each an artificial neural network.

13. A method for analyzing data related to an unidentified biological agent to identify the unidentified biological agent, the method comprising:
    receiving collision induced dissociation data on the biological composition of the unidentified biological agent contained in a sampled material, wherein said collision induced dissociation data includes at least some of the data that would be obtained from a full-scan MS analysis of the unidentified biological agent and at least some of the data that would be obtained from an MS/MS analysis of the unidentified biological agent;
    wherein said collision induced dissociation data relates to multiple ions of different masses;
    first applying a machine learning procedure to said collision induced dissociation data to facilitate the identification of the unidentified biological agent in the sampled material by eliminating at least one group of known biological agents from at least two different groups of known biological agents that may include the unidentified biological agent, wherein at least one of said at least two different groups of known biological agents includes a plurality of sub-groups of biological agents; and
    second applying, following said first applying step, a different machine learning procedure to said collision induced dissociation data relative to said machine learning procedure utilized in the first applying step, wherein said different machine learning procedure is chosen based upon the elimination of said at least one group of known biological agent in the first applying step and provides a more refined identification of the unidentified biological agent than the machine learning procedure utilized in the first analyzing step.

14. A method, as claimed in claim 13, wherein:
    said step of receiving includes receiving collision induced dissociation data on the biological composition of the unidentified biological agent, where the unidentified biological agent is in the form of a bioaerosol.

15. A method, as claimed in claim 13, wherein:

said step of first applying a machine learning procedure includes employing a neural network.

16. A method, as claimed in claim 13, wherein:

said step of first applying a machine learning procedure includes employing multi-variate statistical analysis.

17. A method, as claimed in claim 13, further comprising:

second applying one or more different machine learning procedures to said collision induced dissociation data until an identification of one biological agent is obtained.

* * * * *

UNITED STATES PATENT AND TRADEMARK OFFICE
CERTIFICATE OF CORRECTION

PATENT NO. : 6,799,119 B1
DATED : September 28, 2004
INVENTOR(S) : Voorhees et al.

It is certified that error appears in the above-identified patent and that said Letters Patent is hereby corrected as shown below:

Drawings,
Delete Informal Sheet 7 of 9, and insert formal Sheet 7 of 9 (see attached page).

Column 2,
Line 59, delete "is type", and insert -- is a type --;

Column 3,
Lines 38, 46 and 59, delete "full-CD", and insert -- full-CID --;
Line 40, delete "agent The", and insert -- agent. The --;
Line 52, delete "mix-CD", and insert -- mix-CID --;

Column 5,
Line 53, delete "Mix-CD", and insert -- Mix-CID --;
Line 64, delete "Full-CD", and insert -- Full-CID --;

Column 7,
Line 50, delete "(I)", and insert -- (1) --;
Line 51, delete "bacteria if", and insert -- bacteria. If --;

Column 8,
Lines 11 and 39, delete "ion", and insert -- 1 on --;
Line 67, delete "approaching on", and insert -- approaching 1 on --;

Column 9,
Line 1, delete "from0", and insert -- from 0 --;
Line 56, delete "*Y: pestis*", and insert -- *Y. pestis* --;

Column 10,
Line 44, delete "*ssp;*", and insert -- *spp;* --;

UNITED STATES PATENT AND TRADEMARK OFFICE
CERTIFICATE OF CORRECTION

PATENT NO.    : 6,799,119 B1
DATED         : September 28, 2004
INVENTOR(S)   : Voorhees et al.

It is certified that error appears in the above-identified patent and that said Letters Patent is hereby corrected as shown below:

Column 11,
Line 11, delete "Grain-negative", and insert -- Gram-negative --; and Column 12,
Line 45, delete "between-two", and insert -- between two --.

Signed and Sealed this

Twenty-seventh Day of September, 2005

JON W. DUDAS
*Director of the United States Patent and Trademark Office*